US008201944B2

(12) United States Patent
Vogelsang et al.

(10) Patent No.: US 8,201,944 B2
(45) Date of Patent: Jun. 19, 2012

(54) METHOD, DEVICE AND ARRANGEMENT FOR MEASURING THE DYNAMIC BEHAVIOR OF AN OPTICAL SYSTEM

(75) Inventors: Hartmut Vogelsang, Jena (DE); Michael Bergt, Weimar (DE); Manfred Dick, Gefell (DE); Holger Maeusezahl, Jena (DE); Eckhard Schroeder, Eckental (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 12/860,223

(22) Filed: Aug. 20, 2010

(65) Prior Publication Data

US 2011/0205488 A1 Aug. 25, 2011

Related U.S. Application Data

(63) Continuation of application No. 12/141,757, filed on Jun. 18, 2008, now Pat. No. 7,789,514, which is a continuation of application No. 10/494,784, filed as application No. PCT/EP02/09590 on Aug. 28, 2002, now Pat. No. 7,401,919.

(30) Foreign Application Priority Data

Nov. 7, 2001 (DE) .................................. 101 54 194

(51) Int. Cl.
*A61B 3/00* (2006.01)

(52) U.S. Cl. ........ 351/246; 351/205; 351/211; 351/212; 351/247

(58) Field of Classification Search .................. 351/200, 351/205, 206, 208–212, 221, 236, 237, 246, 351/247; 600/558
See application file for complete search history.

(56) References Cited

U.S. PATENT DOCUMENTS

| 5,963,300 | A | 10/1999 | Horwitz |
| 6,002,484 | A | 12/1999 | Rozema et al. |
| 6,155,684 | A | 12/2000 | Bille et al. |
| 6,264,328 | B1 | 7/2001 | Williams et al. |
| 6,409,345 | B1 | 6/2002 | Molebny et al. |
| 6,550,917 | B1 | 4/2003 | Neal et al. |
| 6,669,341 | B2 * | 12/2003 | Wirth ............................ 351/211 |
| 6,827,442 | B2 | 12/2004 | Ross et al. |

(Continued)

FOREIGN PATENT DOCUMENTS

DE 4222395 1/1994

(Continued)

OTHER PUBLICATIONS

C. Chao et al. "Dynamic Retinal Image Reconstruction of the Human Eye". Fifth International Symposium on Signal Processing and its Applications, ISSPA '99, Brisbane, Australia, Aug. 22-25, 1999, pp. 919-922.

(Continued)

*Primary Examiner* — Huy K Mai
(74) *Attorney, Agent, or Firm* — Leydig, Voit & Mayer, Ltd.

(57) ABSTRACT

A method for measuring the dynamic behavior of an optical system is aimed at rendering the dynamic behavior of the optical system objectively detectable. To this end, the optical system to be measured is stimulated by stimuli whereby causing it to react, and the reaction is detected by means of a wave front analysis.

20 Claims, 2 Drawing Sheets

U.S. PATENT DOCUMENTS

| | | | |
|---|---|---|---|
| 7,401,919 B2 | 7/2008 | Vogelsang et al. | |
| 2003/0071967 A1* | 4/2003 | Campin et al. | 351/211 |
| 2004/0119942 A1* | 6/2004 | Applegate et al. | 351/206 |
| 2005/0225725 A1 | 10/2005 | Warden et al. | |

FOREIGN PATENT DOCUMENTS

| | | |
|---|---|---|
| DE | 4419489 | 12/1995 |
| DE | 19950792 | 4/2001 |
| JP | 03188826 | 8/1991 |
| JP | 00238903 | 9/1997 |
| JP | 2001000395 | 1/2001 |
| WO | 9927334 | 6/1999 |
| WO | 0019885 | 4/2000 |
| WO | 0128408 | 4/2001 |

OTHER PUBLICATIONS

Hofer et al, "Dynamics of the eye's wave aberration", Opt. Soc. Am. A. 2001; 18(3):497-505: XP-001041247.

Navarro et al., "Phase plates for the wave-aberration compensation in the human eye", Opt. Soc. Am. A. 2000; 25 (4):236-238; XP-000947124.

Huang et al., "Dynamic modeling and identification of an adaptive optics system", Control Applications, Proceedings of the 4th IEEE conference on Albany, NY, USA, IEEE 1995: 456-463; ISBN 0-7803-2550-8.

Enrique J. Fernandez et al. "Closed-ILop Adaptive Optics in the Human Eye", Optics Letters, vol. 26, No. 10, May 15, 2001, pp. 746-748.

* cited by examiner

METHOD, DEVICE AND ARRANGEMENT FOR MEASURING THE DYNAMIC BEHAVIOR OF AN OPTICAL SYSTEM

CROSS-REFERENCE TO RELATED APPLICATIONS

This application is a continuation of U.S. patent application Ser. No. 10/494,784, which is a U.S. National Stage Application under 35 U.S.C. §371 of PCT International Application No. PCT/EP02/09590, filed Aug. 28, 2002, which claims priority to German Patent Application No. DE 101 54 194.5, filed Nov. 7, 2001. Each of these applications is incorporated herein by reference as if set forth in its entirety.

BACKGROUND

The present invention relates to a method, device and arrangement for measuring the dynamic behavior of an optical system.

Analysis of optical wavefronts of imaging and laser systems has become increasingly important because it is the starting point for improving the quality of these systems. The availability of commercial Shack-Hartmann sensors (such as SCLA series, WavefrontSciences, http://wavefrontsciences.com) allows aberrations to be detected very accurately and classified in the form of Zernike polynomials of different orders, or alternative representations.

Higher aberrations can also be measured using other aberrometers, including those according to the Tscherning principle, according to Abbe, or the Tracey (ray-tracing) aberrometer, or systems according to the skiascope principle.

Systems that are equipped with a CCD chip for storing the relevant optical information, such as Shack-Hartmann sensors, allow data acquisition to be carried out with video image frequencies, thus enabling dynamic processes to be recorded at a sufficient rate.

There are known methods for correcting also the higher aberrations of third order and higher according to the Seidel or Zernike classification, these methods going beyond the normal spherical correction and cylindrical correction of aberrations. These methods use, for example, adaptive optics, which act in reflection as deformable minors, or liquid crystal optics acting in transmission. These adaptive optics are technologically complex and presently not yet fully developed in all aspects. At present, these optics achieve two-dimensional resolutions of typically several square millimeters, and are already used under laboratory conditions in closed-loop methods to influence wavefronts between the wavefront measurement and the adaptive element (see Fernandez, E. J. Iglesias, I., Artal, P. "Closed Loop Adaptive Optics in the Human Eye", Optics Letters, Vol. 26, No. 10, May 15, 2001). These systems have not been used so far besides and beyond the mere correction of aberrations to carry out real dynamic analyses while varying the most different visual conditions.

Furthermore, especially for ophthalmologic applications, methods have been shown by which wavefronts that are deformed by the optical system of the eye are corrected to an ideal value by integrally taking into account higher-order aberrations (see Optics Letters, Vol. 25 No. 4/Feb. 15, 2000, 236-238, AWACS—Asclepion Wavefront Aberration Correction Simulator—a company document for presentation at the ESCRS in Brussels, September 2000 and at the AAO in Dallas, October 2000).

SUMMARY OF THE INVENTION

An object of the present invention is to provide a method, device and arrangement for objectively determining the dynamic behavior of an optical system.

The present invention provides a method for measuring the dynamic behavior of an optical system, in which the optical system to be measured is stimulated to respond, and the response is determined by a wavefront analysis.

The dynamic behavior of the optical system encompasses, in particular, processes of adaptation to changed visual conditions, for example, accommodation or aperture adjustment (adaptation). The optical system may be an eye, such as a human eye, an artificial eye, or any other artificial device. The stimulus may, in principle, be of any nature. The response is the dynamic behavior of the optical system following the stimulus. The wavefront analysis may be carried out using an aberrometer, in particular, using Shack-Hartmann sensors, but also using aberrometers according to the Tscherning principle, according to Abbe, with a ray tracing aberrometer, or a system according to the skiascope principle. In the case of accommodation, it is possible, in particular, to determine the current focus at any one time as well as its variation over time. It is also possible to determine different iris adjustments in terms of their variation over time. In this connection, the dynamic behavior may also be examined, for example, under the influence of medication.

One embodiment of the method proposes that the stimuli be visual and/or mechanical and/or electrical and/or chemical stimuli. Variable visual stimuli may be produced, for example, using actively controllable light sources, illuminated representations, or the like. In particular, the sharpness of the image and/or the object distance and/or the focus thereof and/or the intensity of the visual stimulus may be varied so as to cause the optical system to undergo accommodation or iris adjustment (adaptation). An aberration of even higher order, for example, in the form of a suitably "deformed" object wavefront may also be used as the visual stimulus. Variable mechanical stimuli may be produced, for example, as an air draft using a blower. Variable chemical stimuli may be produced, for example, by smoke or by introducing a liquid, a gas, or an aerosol. Administration of medication is also possible. Variable electrical stimuli may be achieved using electrodes applied directly to the eye or in the area of the eye, or by an electrical signal inductively or capacitively coupled in. The above-mentioned stimuli may be applied alone or in any combination, and be varied either abruptly or continuously.

In one embodiment of the method, the optical system to be measured is a human eye. It is an aim of the method aims to stimulate an individual eye or the eye system in the visual process in order to selectively produce an excitation and an associated influence on the eye parameters. The induced changes in the eye parameters directly change the imaging properties of the eye and are therefore accessible, for example, via a wavefront measurement triggered synchronously with the excitation. This method allows analysis and measurement of the most different effects. For example, the time dependence and speed of accommodation and of the accommodative capacity, the adaptation and adaptive capacity or adaptation speed of the eye may be examined under influences such as aberration, illumination, medication, or psychic influences. The dynamic short- and long-time behavior of contact lenses, such as slippage or the like, may be examined with respect to the changes in aberration due to wearing of contact lenses. It is possible to determine the dynamic behavior of intraocular lenses (IOL) and accommodative intraocular lenses, and the reciprocal effect of the residual ciliary body on intraocular lenses, as well as the fit and movement and, possibly, the induced accommodation thereof. Also possible are connections between the physical vision and the brain performance which may possibly help discover objective conclusions about clinical pictures such as headaches due to overstress. Thus, for example, it is possible to measure dazzling effects and other time-variant effects in connection with fatigue phenomena during motoring. Dynamic optical correction may be examined, for example, in relation to occupational groups, i.e., in terms of specific visual requirements.

In a refinement of the method, it is proposed to synchronize the stimulation of the eye to be measured with the aberrometer. This allows the measured adaptation processes of the eye to be directly associated with the particular stimulus and its variation over time. In the process, the synchronization can be carried out, for example, temporally or with respect to the intensity between the particular stimulus and the aberrometry measurement.

When carrying out the method, it is possible to stimulate one or both of the human eyes to respond. Similarly, it is possible to measure one or both of the human eyes. Based on the dynamic measurement results obtained by stimulation, optimized/averaged values for static/stationary correction of the wavefront may be derived for the specific eye that has been measured. This makes it possible to provide the eye with an optimal wavefront correction for its specific action spectrum. It is also possible to provide solutions tailored to specific visual processes. Examples to be mentioned include night vision, speed-optimized accommodation, or close and distant vision.

The present invention also provides a device for measuring the dynamic behavior of an optical system, in particular, of a human eye, including a stimulation unit and an aberrometer. Using the stimulation unit, the optical system to be examined may be selectively caused to adapt to external stimuli. For this purpose, the stimulation unit is designed such that it can exert these external stimuli on the optical system. Possible external stimuli include, in principle, all physical or chemical effects or means that produce an adaptive response of the optical system. The stimulation unit may act on the optical system abruptly and/or continuously, and be disposed in front of either the unmeasured optical system or the optical system to be measured. Here, "aberrometers" are generally understood to mean devices for wavefront measurement or aberration measurement. These may include both devices with electronic data acquisition and manually operable devices.

A particularly simple and, moreover, automated way of evaluating the optical data is possible if the aberrometer includes a wavefront analysis device. The wavefront analysis device may be, for example, a Shack-Hartmann sensor equipped with a CCD chip for storing the relevant optical information.

The measurement results, and thus the result of the dynamic adaptation process, may be graphically visualized by transferring the data to a software application.

It is particularly advantageous if the stimulation unit is able to trigger a visual and/or mechanical and/or electrical and/or chemical stimulus. In particular, a visual stimulus may be designed to cause the optical system to undergo accommodation or iris adjustment. Thus, different stimuli may be exerted on the eye, thus also allowing simulation of everyday situations, such as an air draft or chemical stimuli caused by smoke, or the like.

The stimulation unit may be disposed in front of the eye that looks past the aberrometer or, alternatively, the beam path of the stimulation unit may be reflected into the aberrometer. In the first-mentioned embodiment of the device, the eye not to be examined may be stimulated whereas in the second-mentioned embodiment, the eye to be examined may be directly stimulated by external stimuli.

Alternatively, the stimulation unit may be integrated into the aberrometer. In this case, the beam path of the stimulation unit is directly coupled into that of the aberrometer in a common housing. This enables a very compact design.

The device may be designed for both monocular and binocular vision. Similarly, the stimulation may affect one or both eyes. Therefore, eye measurement and eye stimulation may be implemented in any combination, for example, stimulation of one eye and measurement of the other eye, stimulation of one eye and measurement of the same eye, stimulation of one eye and measurement of both eyes, stimulation of both eyes and measurement of one or both eyes.

In a preferred embodiment, it is proposed that the stimulation unit include a fixation object. The subject has to fixate the fixation object, thus causing the eye to focus in a defined manner. The fixation object is a pictorial representation that is easily recognizable by the subject, or a defined light spot. Here, it is preferred to use a finely patterned image, or a light source composed of a plurality of elements which may, for example, be graduated in color.

It is advantageous if the fixation object is able to emit a light stimulus that is variable in intensity and/or focus. The eye focusing the fixation object may be stimulated directly in this manner. The change in intensity may be achieved, for example, by changing the luminosity when using light sources as the active elements, or by changing the illuminance when using passive elements such as an illuminated graphic. A change in focus is possible, for example, by moving the fixation object itself, or by changing lenses disposed in front thereof.

The fixation object is preferably an illuminated graphic. This is an object which can be easily and reliably recognized and fixated by the subject and which, moreover, is easy to implement.

The device may include at least one phase plate that is insertable into the beam path of the stimulation unit and/or of the aberrometer. Advantageously, a set of phase plates is used, which are sorted by the different Zernike polynomials with graded amplitudes, and which may be positioned in front of the system to be examined, similarly to the trial lenses in the known phoropter. Possible phase plates include, for example, transparent glass or plastic plates whose surfaces are patterned in such a manner that defined aberrations, for example, according to a single Zernike term, are superimposed on a light wave that passes through the plate. A changing device, preferably a turret changer, preferably contains plates of one order of the Zernike coefficients with different amplitudes. By providing several such changing devices one behind the other in a centered arrangement, it is possible to rotate different phase plates into the optical visual axis of the optical system to be examined Thus, a finely gradable combination of higher-order aberrations may be placed on the optical visual axis of the optical system to be examined. This arrangement allows, in particular, visual defects that are due to higher-order aberration to be subjectively assessed after an adapted stationary state, for example of the human eye, has been reached. The assessment may be carried out using a time scale, for example, after several seconds of adaptation.

The device may include software for evaluating the differently stimulated dynamic measurement data of the eye, the software providing an optimal or average wavefront value, which is used for static/stationary correction of the optical defects of vision in the known correction methods (spectacles, CL, IOL, LASIK, PRK, . . . ).

The present invention also provides an arrangement for measuring the dynamic behavior of an optical system, in particular, of an eye, including an aberrometer and a stimulation unit. In this arrangement, the elements previously implemented together in the device are separated. Therefore, it is also possible to use a conventional device for measuring the aberration of an eye together with an independent stimulation unit. The present invention also provides the use of a device described herein for measuring the dynamic behavior of an optical system.

BRIEF DESCRIPTION OF THE DRAWINGS

Advantageous embodiments of the present invention will be further explained with reference to the drawing, in which.

DETAILED DESCRIPTION

Figure 1:
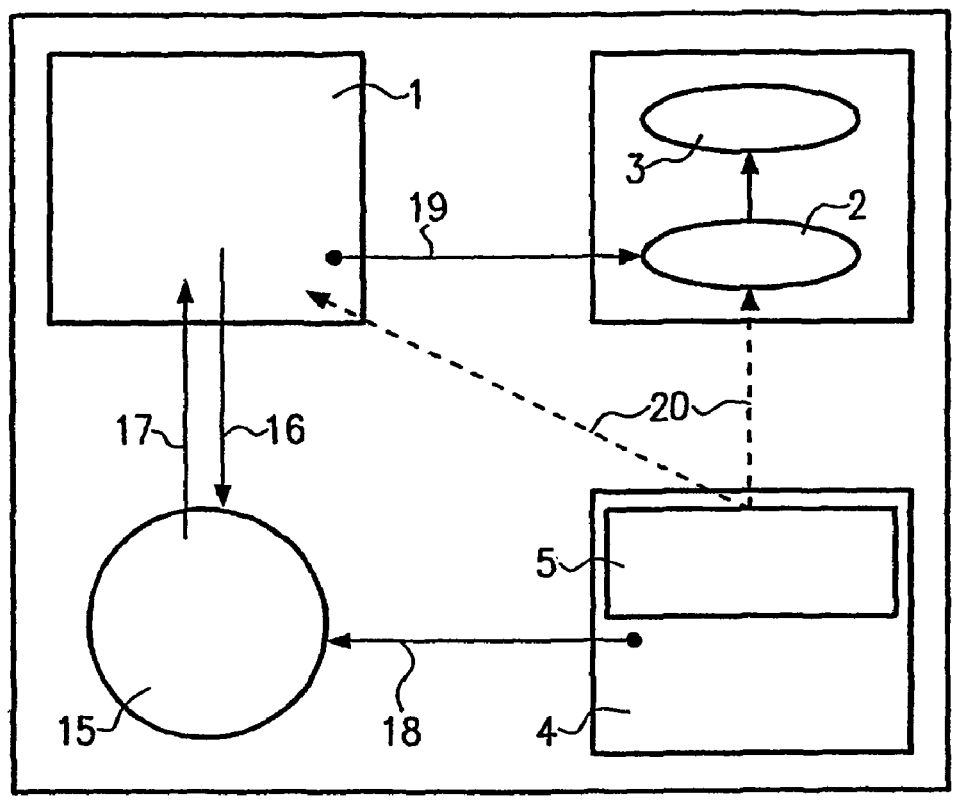
FIG. 1 is a schematic diagram of a device for carrying out the method.

Reference is first made to FIG. 1, which is a schematic diagram of a device and the associated method sequence for dynamic stimulation and dynamic measurement of the aberrometry of an eye 15. The Figure shows the individual components and their operative connection. The device includes a unit for measuring the wavefront/aberrometry of eye 15, the unit being able to measure either both eyes at the same time or one eye at a time. In the latter case, the eye that is currently not being measured, may either look with an unrestricted view past the unit, or also look into the unit. For the sake of simplicity, the unit for measuring the wavefront/aberrometry of an eye will be referred to as "aberrometer 1" hereinafter. Aberrometer 1 emits measurement light 16 into eye 15, and the eye returns signal light 17. Measurement light 16 and signal light 17 are indicated by arrows in FIG. 1. The device further includes a device for dynamic data acquisition 2 which receives raw data 19 of aberrometer 1. This further device may be a common device for measurement value acquisition, such as a program-controlled computer including software capable, in particular, of acquiring sequential series of measurements in real time. For this purpose, intermediate data storage may be required in a volatile or non-volatile memory, for example, of a control computer. The device further includes analysis software capable of analyzing the acquired data or data sets in order to calculate the determining parameters of the wavefront (for example, Zernike or Taylor coefficients). The measurement results, and thus the result of the dynamic adaptation process, may be graphically visualized by a software application. For this purpose, an analysis module 3 is used to which the acquired data is transferred. The capabilities of dynamic data acquisition 2 and of analysis module 3 may be combined in such a manner that a sequential real-time measurement with simultaneous analysis can be carried out that is adapted to the hardware and possibly reduced in its acquisition rate. Also provided is a stimulation unit 4 for producing an optical influence, for example, aberration, light inflow, object distance, or the like, in an abruptly and/or continuously variable manner. This stimulation unit is disposed in front of either the unmeasured eye 15 or the eye 15 to be measured, and may be synchronized with dynamic data acquisition 2. The stimulation of eye 15 is indicated by an arrow 18 in FIG. 1. A synchronization unit 5 is used for synchronization between stimulation unit 4 and aberrometer 1. The synchronization unit may send synchronization pulses 20 (indicated by dashed arrows in FIG. 1) to the aberrometer and/or the device for dynamic data acquisition 2.

Stimulation of eye may also be accomplished using eye charts and the like without the need for synchronization. Thus, the connection between stimulation unit 4 and aberrometer 1 and/or dynamic data acquisition 2 is thus dispensed with. Aberrometer 1, dynamic data acquisition 2, analysis module 3, and stimulation unit 4 may also be implemented as a unit and thus as a one-part assembly.

Stimulation unit 4 may also be implemented and used as an independent separate unit. The then existing unit is kind of a stimulation phoropter through which the subject may assess, for example, a phase-plate correction with or without variation of other visual parameters. Synchronization unit 5 may then be dispensed with.

Figure 2:
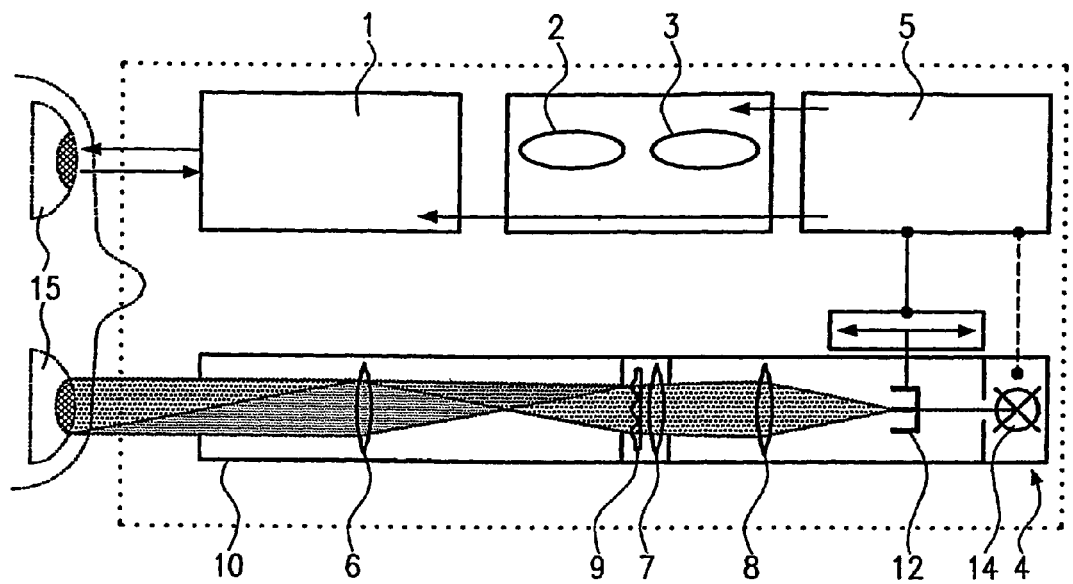
FIG. 2 is a schematic diagram of a first embodiment of the device according to the present invention.
Figure 3:
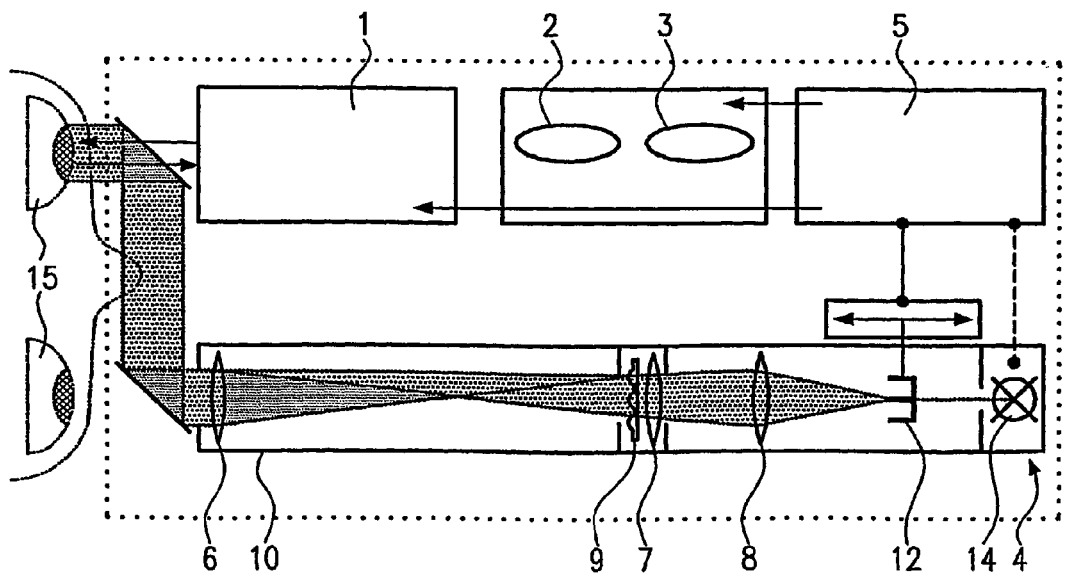
FIG. 3 is a schematic diagram of a second embodiment of the device according to the present invention.

FIGS. 2 and 3 show specific embodiments of the device. The shown beam paths through a first lens 6, a second lens 7, and a third lens 8 do not exactly correspond to the real beam paths when considered within the framework of geometrical optics, but are only intended for purposes of illustration. The practical implementation of the optical concept may be accomplished in such a way that the patient's nose does not constitute an obstacle. In the optical set-up shown in FIGS. 2 and 3, a phase plate 9 is located in a plane conjugate to the corneal surface or spectacle correction surface. By integrating a mechanism (not shown) for automatically changing phase plates 9, for example, in the form of a phase-plate changer wheel or the like, it is also possible to easily produce different aberrations during or between measurement series. A first iris 10 and a second iris 11, together with the fixation at a fixation object 12, define the optical axis. Further aiming devices, such as surface crosses, may also be provided, as the case may be. In addition, the centration may be checked by a video image which may be picked off, for example, by beam splitters inside the device of FIGS. 2 and 3. Varying accommodation states may be stimulated by moving the fixation object along a travel path 13, or alternatively, for example, by moving third lens 8. The adaptation may be influenced through adjustment of the illumination of fixation object 12 by a light source 14. Additionally or alternatively, it is possible to directly adjust brightness of the room light and/or of the ambient light. This option is not shown for the sake of simplicity. The individual components may be controlled and actuated electrically or electromotively. The synchronization of these components with the measurement and the data acquisition may then be easily carried out by querying programmable interfaces.

In the device according to FIG. 2, eye 15 is measured, and the respective other eye 15 is stimulated, while in the device according to FIG. 3, the eye 15 to be measured is stimulated at the same time. First, the common set-up in FIG. 2 will be explained. The device includes an aberrometer 1, which is a unit for measuring the wavefront deformation by the optical system of the eye and thus for determining and classifying the aberrations of eye 15, including also higher-order aberrations. Aberrometer 1 is coupled to a device for dynamic data acquisition 2 which here is a module for controlling aberrometer 1. This module may trigger a wavefront measurement process. It is also possible to store the acquired measurement data intermediately, and to subsequently reconstruct the measured wavefront from the measurement data. For this purpose, it is possible to store, for example, the raw data of the video image of the sensor, or also completely evaluated wavefront parameters such as Zernike coefficients. The measurement and possible evaluation and storage are carried out at clock rates that are faster than the adaptation process to be examined. The clock rates may, for example, be in the range of 10 to 100 Hz.

The device for dynamic data acquisition 2 is coupled to an analysis module 3. Analysis module 3 is used for evaluation of the sensor data and, possibly, for reconstruction and graphical visualization of the measured and stored wavefronts, and may substantially be implemented in software. Moreover, it is possible to parameterize the wavefront, for example, through expansion by Zernike polynomials, or by zonal reconstruction. The analysis process may be coupled in close coupling with the device for dynamic data acquisition 2, and perform the analysis process partially or completely before intermediate storage.

A stimulation unit 4 is essentially composed of an optical system which presents to the eye 15 to be examined or to the free eye 15 a visual object to be fixated which has a defined pattern, and which induces eye 15 to focus on the pattern of the object. Stimulation unit 4 may contain optical elements, such as lenses or phase plates, which deform the wavefront originating from the visual object before it enters the eye. Eye 15, which tries to obtain a sharp image of the visual object, may thus be stimulated to undergo adaptive responses within the optical system. Preferably, the imaging properties of stimulation unit 4 may be varied over time to produce a dynamic response of eye 15. Stimulation unit 4 may send information about its current state to a synchronization unit 5 with the wavefront measurement.

Synchronization unit 5 is a module for synchronizing dynamic changes in stimulation unit 4 with the device for dynamic data acquisition 2. The aim is to correlate the measured wavefront data with the respective states of the synchronization unit.

The embodiments of an aberrometer 1 shown in FIGS. 2 and 3 may be referred to as "dynamic stimulation aberroscopes". Here, it should be noted that the optical concept may be implemented in such a manner that, unlike in the diagram, the unmeasured eye does not have to be restricted in its view, but may look with an unrestricted view. In a simplified variant, it would be possible to dispense with the synchronization between stimulation unit 4 and aberrometer 1 and device for dynamic data acquisition 2. In further variants, an eye chart that is stationary or movable for varying the distance and/or a phase-plate phoropter are used for stimulation instead of an integrated fixation object.

The embodiment of a stimulation unit 4 shown in FIG. 2 is also to be regarded as an improvement to the simple phase-plate phoropter, and may be designed as a stand-alone device to include, for example, correction of the aberration and a simple eye chart as the fixation object, etc., in the different variants.

To selectively superimpose aberrations on the object wavefront, it is optionally possible to insert an adaptive optical element instead of a phase plate and/or the imaging optics according to FIGS. 2 and 3. The thereby stimulated dynamic changes in the imaging properties of eye 15 are dynamically determined by aberrometer 1 in a time sequence which may be synchronized with the variation of the imaging properties by the adaptive optics. Transmission-based adaptive elements, such as liquid-crystal phase modulators, may be mounted in the arrangement according FIGS. 2 and 3 instead of, for example, the phase plate in a similar manner.

Although the use of an adaptive optic additionally requires an electronic control of the adaptive optic and is therefore more complicated, it offers stimulation options which would not be possible, or only with difficulty, using devices with phase plates. Depending on the control speed of the adaptive optical elements, it is possible to dynamically change or to selectively apply arbitrary aberrations of the object wavefront.

Stimulation unit 4 is designed as an optical system which is placed either in front of the eye 15 that is unrestricted in its view, or is reflected into the beam path of the eye examined by the aberrometer, as shown in FIG. 3, or stimulation unit 4 is integrated into aberrometer 1. In the case of the latter embodiment, again, two variants are possible: stimulation unit 4 may act on the measured eye or eyes 15, or on the unmeasured eye 15.

The stimulation unit itself is an optical device, in which a fixation object is placed in front of the measured eye or eyes, or the eyes that are unrestricted in their view, and whose center is to be fixated and focused by the respective eye during the examination. The optical action during stimulation may be modulated either abruptly or continuously, which is achievable, for example, by changing the distance, luminance etc., of the fixation object, and/or by mounting phase plates. All optically effective modifications may be combined in any way. If the optical action is synchronized, for example, in terms of time or illumination, with the dynamic measurement of eye 15 by aberrometer 1, then the devices embodied according to FIGS. 2 and 3 are obtained. Synchronization of the action is not necessarily required. Information about the dynamic responses of the eye or eyes may also be measured in an unsynchronized manner. To this end, it is possible to associate the measured values temporally, for example, via the knowledge of the data acquisition frequency of the device for dynamic data acquisition 2. The measured values may be provided with a time stamp, for example, when electronically stored on a data carrier or the like. The device for dynamic data acquisition 2 and analysis module 3 may also be combined so as to perform not only dynamic data acquisition, but at the same time also high-speed analysis of the data.

Fixation object 12 may be implemented, for example, by an illuminated graphic having a sufficiently fine pattern, but may also be a simple eye chart positioned separately.

The imaging of fixation object 12 may be accomplished by swinging in optical elements such as lenses, and may possibly be checked via a video system. The centration with respect to a predetermined line of sight may be optimized by iris systems. For example, an automatic positioning means makes is possible to selectively produce accommodation states by varying distances between the optical components and/or the fixation object. Suitable adjustment of the illumination of the fixation object and/or of the room light leads to defined adaptation adjustments, which may also be kept variable and which form additional measurement parameters.

By inserting specially prepared phase plates with defined surface topography into the beam path of stimulation unit 4 and/or of aberrometer 1, the device allows aberrations to be selectively applied to eye or eyes 15. To this end, the phase plates may be disposed in a turret changer (not shown here) and able to be inserted into the beam path of stimulation unit 4 and/or of aberrometer 1 individually or in combination.

The above-described device and the method which can be carried out with it are used for selective visual stimulation of a biological or artificial eye 15 and for determining the associated dynamic adaptation process of the optical visual apparatus by measuring the wavefront aberration. The visual stimulation produced when viewing into or through a suitable apparatus produces an influence on the imaging properties of eye 15; this influence being simultaneously measurable in real time and in time synchronization with the stimulation using a wavefront analysis system or aberrometer 1. This enables completely new ways of diagnosis, making the dynamics of adaptation processes of eye 15 accessible. To this end, visual conditions, such as object distance and brightness are modified and specific aberrations are selectively corrected and/or introduced, in particular, simultaneously. This makes it possible, for example, to study the influence of specific aberration terms on the accommodative capacity, or to examine whether an implantable intraocular lens is capable of accommodation in virtue of the residual ciliary body, and how this may possibly be used in an optimal manner. A further advantage of the present invention is that it allows personal impressions of a subject during the assessment of dynamic visual processes to be correlated with physically objective measurement data.

Using the device and method, it is possible to stimulate dynamic changes in the imaging properties of the eye, and to record their variation over time. A system of optical elements allows to selectively compensate for existing aberrations of even higher order, and to selectively introduce other aberrations for stimulation to determine the influences on the dynamics of the optical system of eye 15. This allows the most different dynamic processes, such as during accommodation or adaptation, to be documented in an image sequence or video recording of the development of the wavefront aberrations, from which it is possible to derive dynamic parameters, such as adaptation range, times, speeds, or accelerations, for example, during accommodation or adaptation. In this manner, conclusions about anatomical parameters, such as the elasticity of the eye lens, which may be connected, for example, with questions of the interaction of the deformation of the eye lens and cornea and the dynamics of intraocular lenses, or also the primary response capacity of the eye, become objectively measurable. It is possible to discover fundamental relationships of the effect of medication or, for example, cause-effect relationships of clinical pictures such as headaches, fatigue, and overstress.

The described invention allows objective dynamic measurement of the imaging properties of the eye during selectively stimulated adaptation processes under predefined boundary conditions.

What is claimed is:

1. A method for measuring a change in imaging properties of an optical system, the method comprising:
    stimulating the optical system so as to selectively produce an excitation and an associated influence on the optical system; and
    performing a wavefront measurement over time so as to measure the change in the imaging properties of the optical system induced by the excitation.

2. The method according to claim 1, wherein the optical system is a human eye.

3. The method according to claim 1, wherein the wavefront measurement is performed synchronously with the excitation.

4. The method according to claim 1, wherein the measured change in the imaging properties of the optical system includes a measured change in at least one of a time dependence and speed of accommodation, accommodation capacity, accommodation speed, adaptation, adaptive capacity and adaptation speed of the optical system under the associated influence.

5. The method according to claim 4, wherein the associated influence includes at least one of an aberration, an illumination, a medication and a psychic influence.

6. The method according to claim 1, wherein the optical system is a human eye including a contact lens and the measured change in the imaging properties of the optical system includes a measured change in aberration.

7. The method according to claim 6, further comprising determining a behavior of the contact lens based on the measured change in aberration.

8. The method according to claim 7, wherein the behavior of the contact lens is slippage.

9. The method according to claim 1, wherein the optical system includes an intraocular lens and the measured change in the imaging properties of the optical system includes a reciprocal effect of residual ciliary body on the intraocular lens.

10. The method according to claim 9, further comprising determining at least one of a fit, a movement and an induced accommodation of the intraocular lens based on the measured change in the imaging properties of the optical system.

11. The method according to claim 1, wherein the optical system includes a human eye and further comprising determining a brain performance in connection with the measured change in the imaging properties of the human eye.

12. The method according to claim 11, wherein the determined brain performance is used to determine a clinical picture.

13. The method according to claim 12, wherein the clinical picture is a headache due to overstress.

14. The method according to claim 11, wherein the measured change in the imaging properties of the human eye includes a time-variant effect of fatigue phenomena during motoring.

15. The method according to claim 14, wherein the time-variant effect is dazzling.

16. The method according to claim 1, further comprising evaluating a dynamic optical correction in relation to a specific visual requirement of an occupational group.

17. A system for measuring a change in imaging properties of an optical system, the system comprising:
    a stimulation unit configured to selectively produce an excitation and an associated influence on the optical system; and
    an aberrometer configured to perform a wavefront measurement over time on the optical system so as to measure the change in the imaging properties of the optical system induced by the excitation.

18. The system according to claim 17, wherein the optical system is a human eye.

19. The system according to claim 17, wherein the aberrometer is configured to perform the wavefront measurement synchronously with the excitation.

20. A method of measuring a change in eye parameters comprising:
    inducing the change in the eye parameters by stimulating a human eye so as to produce an excitation; and
    measuring the induced change in the eye parameters using a wavefront measurement trigger synchronously with the excitation.

* * * * *